United States Patent
Newman et al.

(10) Patent No.: US 10,599,164 B2
(45) Date of Patent: Mar. 24, 2020

(54) DETERMINATION OF SUBSTANCE PRESENCE, IDENTITY AND/OR LEVEL IN VESSELS

(71) Applicant: Halliburton Energy Services, Inc., Houston, TX (US)

(72) Inventors: Katerina V. Newman, Houston, TX (US); Dale E. Jamison, Humble, TX (US); Cato Russell McDaniel, The Woodlands, TX (US); Xiangnan Ye, Cypress, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 178 days.

(21) Appl. No.: 15/128,768

(22) PCT Filed: Jun. 12, 2014

(86) PCT No.: PCT/US2014/042183
§ 371 (c)(1),
(2) Date: Sep. 23, 2016

(87) PCT Pub. No.: WO2015/191074
PCT Pub. Date: Dec. 17, 2015

(65) Prior Publication Data
US 2017/0160754 A1  Jun. 8, 2017

(51) Int. Cl.
*G05D 11/13* (2006.01)
*G01N 25/18* (2006.01)
(Continued)

(52) U.S. Cl.
CPC ....... *G05D 11/132* (2013.01); *B01D 17/0208* (2013.01); *G01F 1/007* (2013.01);
(Continued)

(58) Field of Classification Search
CPC ... B01D 17/0208; G01F 1/007; G01F 23/247; G01N 25/18; G05D 11/132;
(Continued)

(56) References Cited

U.S. PATENT DOCUMENTS

| | | | | |
|---|---|---|---|---|
| 3,181,557 A | * | 5/1965 | Lannan, Jr. | G01F 23/247 137/391 |
| 4,065,760 A | * | 12/1977 | Feldon | G01F 23/247 338/22 SD |

(Continued)

FOREIGN PATENT DOCUMENTS

| | | |
|---|---|---|
| JP | 10-43572 A | 2/1998 |
| JP | 10043572 A | 2/1998 |

(Continued)

OTHER PUBLICATIONS

"Machine Translation of KR 10-1998-030379A, published Jul. 25, 1998", 9 pgs.

(Continued)

*Primary Examiner* — William M McCalister
(74) *Attorney, Agent, or Firm* — Chamberlain Hrdlicka

(57) ABSTRACT

A process control system can include a vessel, and at least one heat transfer property sensor that measures a heat transfer property of a substance at the vessel. The process control system can also include a monitoring device that receives an output of the heat transfer property sensor, and a process control device that is adjusted in response to the heat transfer property sensor output. A method of controlling a process can include measuring a thermal conductivity of a substance at a vessel, and adjusting the process in response to the measuring.

18 Claims, 6 Drawing Sheets

(51) Int. Cl.
*G01F 23/24* (2006.01)
*B01D 17/02* (2006.01)
*G01F 1/00* (2006.01)

(52) U.S. Cl.
CPC .......... *G01F 23/247* (2013.01); *G01N 25/18* (2013.01); *G05D 11/135* (2013.01)

(58) Field of Classification Search
CPC ............... G05D 11/135; Y10T 137/27; Y10T 137/2534; Y10T 137/7303
USPC ................. 137/101.25, 87.02, 391
See application file for complete search history.

(56) References Cited

U.S. PATENT DOCUMENTS

| | | | | |
|---|---|---|---|---|
| 4,326,199 | A * | 4/1982 | Tarpley | G08B 21/182 137/386 |
| 5,421,202 | A * | 6/1995 | Le Pimpec | G01F 23/247 338/28 |
| 2002/0144994 | A1* | 10/2002 | Golan | G01N 25/18 219/505 |
| 2007/0178020 | A1* | 8/2007 | Atlas | G05D 23/1919 422/105 |
| 2009/0294271 | A1 | 12/2009 | Holmberg et al. | |
| 2012/0180877 | A1* | 7/2012 | Pallais | G01M 3/002 137/487.5 |
| 2012/0260998 | A1* | 10/2012 | Rodgers | G01G 17/06 137/14 |
| 2012/0318381 | A1* | 12/2012 | Arensmeier | F24F 13/222 137/395 |
| 2014/0174547 | A1* | 6/2014 | Joo | D06F 39/087 137/2 |
| 2014/0202714 | A1* | 7/2014 | Burkhart | A62C 35/62 169/9 |
| 2014/0261749 | A1* | 9/2014 | Chen | E03C 1/057 137/78.1 |

FOREIGN PATENT DOCUMENTS

| | | |
|---|---|---|
| KR | 10-1998-030379 A | 7/1998 |
| KR | 1019980030379 A | 7/1998 |
| KR | 10-0905462 B1 | 7/2009 |
| KR | 100905462 B1 | 7/2009 |
| KR | 1020120101964 A | 9/2012 |
| WO | 2003002244 A1 | 1/2003 |
| WO | WO-2015191074 A1 | 12/2015 |

OTHER PUBLICATIONS

"Machine Translation of KR 10-2012-0101964A, published Sep. 17, 2012", 17 pgs.

"Machine Translation of KR 10-0905462B1, published Jul. 2, 2009", 12 pgs.

"International Application Serial No. PCT/US2014/042183, International Search Report dated Feb. 26, 2015", 3 pgs.

"International Application Serial No. PCT/US2014/042183, Written Opinion dated Feb. 26, 2015", 8 pgs.

* cited by examiner

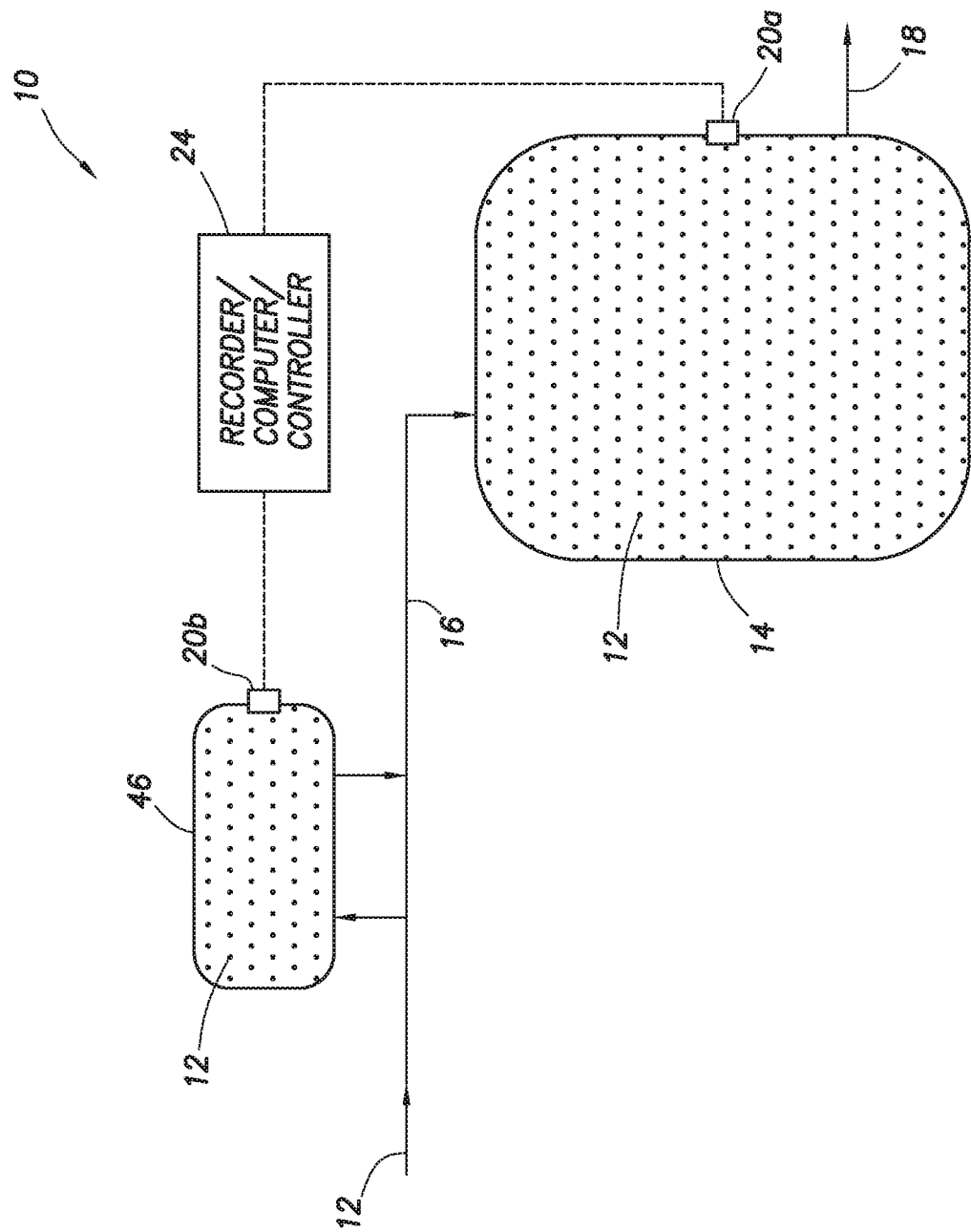

DETERMINATION OF SUBSTANCE PRESENCE, IDENTITY AND/OR LEVEL IN VESSELS

PRIORITY APPLICATIONS

This application is a U.S. National Stage Filing under 35 U.S.C. § 371 from International Application No. PCT/US2014/042183, filed on 12 Jun. 2014 and published as WO 2015/191074 A1 on 17 Dec. 2015, which application and publication are incorporated herein by reference in their entireties.

TECHNICAL FIELD

This disclosure relates generally to equipment and techniques used in process control and, in one example described below, more particularly provides for determination of substance presence, identity and/or level in vessels.

BACKGROUND

In various industries, it can be important to know whether a tank or other vessel contains a substance, a level of the substance in the vessel, and/or an identity of the substance in the vessel. For example, a process (such as, a chemical reaction, a mixing of materials, a supply of material to production equipment, inventorying of materials, etc.) can be significantly affected by an absence of a needed substance, a change in a type of substance present, or a change in an amount of the substance available for the process. Therefore, it will be appreciated that advancements are continually needed in the arts of determining a presence, identity and/or level of a substance in a vessel.

BRIEF DESCRIPTION OF THE DRAWINGS

FIGS. 2-6 are representative schematic views of additional examples of the system and method.

DETAILED DESCRIPTION

Figure 1:
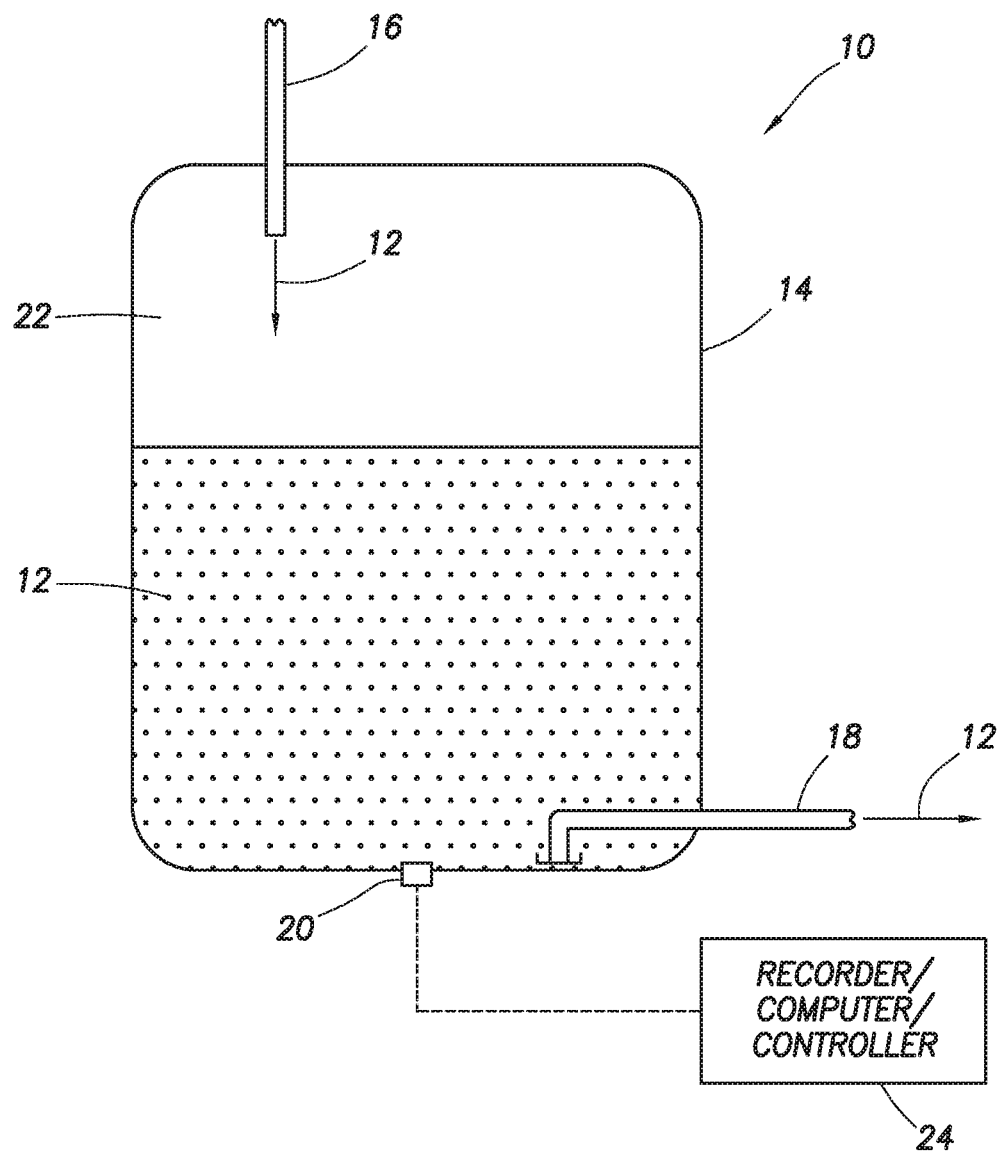
FIG. 1 is a representative schematic view of an example of a system and associated method which can embody principles of this disclosure.

Representatively illustrated in FIG. 1 is an example of a process control system 10 and associated method which can embody principles of this disclosure. However, it should be clearly understood that the system 10 and method are merely one example of an application of the principles of this disclosure in practice, and a wide variety of other examples are possible. Therefore, the scope of this disclosure is not limited at all to the details of the system 10 and method described herein and/or depicted in the drawings.

In the system 10 of FIG. 1, a substance 12 is contained in a vessel 14. The substance 12 may be a solid (such as, particulate, granular or powered material), a liquid, a gas, a vapor, a gel or a mixture of any of these. The vessel 14 is configured to contain the particular substance 12. For example, if the substance 12 is a gas at other than atmospheric pressure, or if the vessel 14 is located in an environment at other than atmospheric pressure (such as, in a well, in another vessel, etc.), then a wall of the vessel 14 can be configured to withstand differential pressure.

The substance 12 may be delivered into the vessel 14 via a conduit 16, and the substance may be discharged from the vessel via another conduit 18. However, the scope of this disclosure is not limited to any particular configuration or technique for delivering the substance 12 into, or discharging the substance from, the vessel 14. In other examples, the substance 12 could be delivered into, and/or discharged from, the vessel 14 by force of gravity, by centrifugal force, by differential pressure, or by any other means.

In the FIG. 1 example, it is desired to determine whether the substance 12 is present in the vessel 14. This determination could, for example, be useful in indicating whether the substance 12 is available for a certain process (such as, a chemical process, mixing with another substance, producing a product, etc.).

A thermal conductivity sensor 20 is used to measure thermal conductivity at a selected location in the system 10. In the FIG. 1 example, the substance 12 collects at a bottom of the vessel 14 (as would be the case if the substance were a solid or liquid), and so the sensor 20 is located in a bottom wall of the vessel. If the substance 12 were a vapor, then the sensor 20 could be otherwise located.

Any suitable thermal conductivity sensor may be used in the system 10. Typically, a thermal conductivity sensor will include a heating element and a temperature sensor for detecting a temperature of a heated substance. However, other types of thermal conductivity sensors may be used, if desired.

The term "thermal conductivity" is used herein to indicate a heat transfer property of a drilling fluid. Other heat transfer properties that could be measured by the sensor 20 include thermal inertia, thermal effusivity and thermal diffusivity. Thus, the scope of this disclosure is not limited to measurement of only thermal conductivity of a substance. Thermal conductivity is merely one example of a heat transfer property that could be measured, evaluated, controlled, etc., using the principles of this disclosure.

In the FIG. 1 example, the heat transfer property sensor 20 provides real time measurements of thermal conductivity. This enables decisions to be quickly made, so that a process can be appropriately controlled as needed, and even automated if desired.

As used herein, the term "real time" is used to indicate immediate performance of an activity. An activity is considered to be performed in real time if the activity is instantaneous or takes no more than a few seconds to perform. An activity that takes many minutes, or an hour or more to perform, is not considered to be performed in real time.

Different substances generally have respective different thermal conductivities. For example, the substance 12 is expected to have a thermal conductivity that is different from a thermal conductivity of another less dense substance 22 (such as a gas, atmosphere, etc.) above the substance 12 in the vessel 14. Thus, if the substance 12 is not present in the vessel 14, so that the sensor 20 is exposed to the substance 22, the thermal conductivity measured by the sensor will be different from the thermal conductivity measured by the sensor when the substance 12 is present in the vessel. In this manner, a monitoring device 24 can determine whether the substance 12 is present in the vessel 14.

If the substance 12 is not present in the vessel 14, and it is desired for the substance to be present in the vessel, then a computer and/or controller of the monitoring device 24 can, for example, cause a flow rate of the substance 12 via the conduit 16 into the vessel 14 to be increased, and/or can cause a flow rate of the substance via the conduit 18 out of the vessel to be decreased, etc. However, the scope of this disclosure is not limited to any particular way of ensuring presence or mitigating absence of the substance 12 in the vessel 14.

Note that it is not necessary for the sensor 20 to be located in a wall of the vessel 14. In some examples, the sensor 20 could be internal to the vessel 14. In other examples, the sensor 20 could be in the conduit 16 or 18 in sufficiently close proximity to the vessel 14 to ensure that, if the substance 12 is in the conduit, it is also in the vessel.

The monitoring device 24 can perform any one or more of a variety of functions. For example, the monitoring device 24 can include a recorder to record thermal conductivity measurements made by the sensor 20, can include a computer to use the thermal conductivity measurements in various algorithms (such as, to determine whether the substance 12 is present, whether there is a change in thermal conductivity, etc.), and can include a controller to control operation of various process control devices in response (such as, to control flow rates of the substance 12 through the conduits 16, 18, etc.).

In some examples, the monitoring device 24 can include a display to show thermal conductivity measurements and/or measurement changes to a user, and can include an alarm to warn the user when appropriate (for example, to warn that the substance 12 is not present in the vessel 14). However, the scope of this disclosure is not limited to use of a monitoring device having any particular function or combination of functions.

Figure 2:
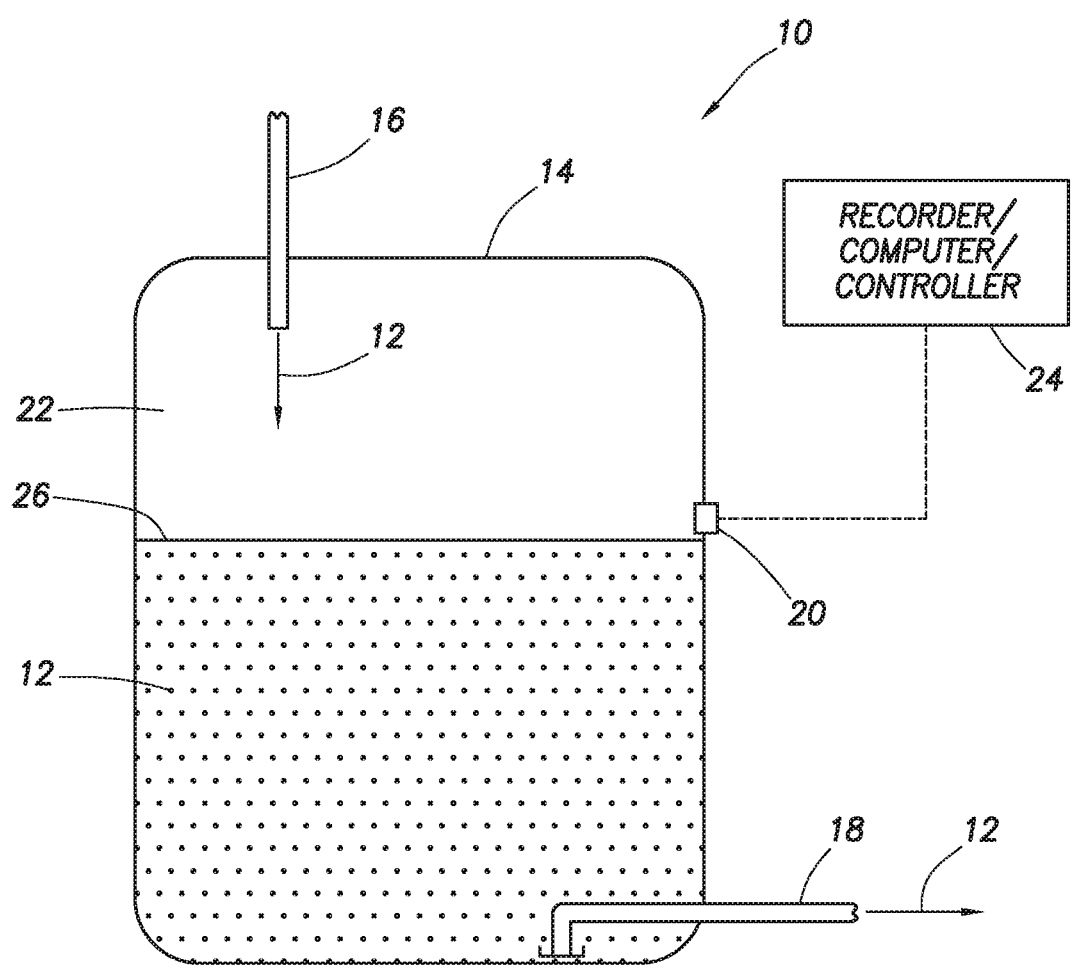

Referring additionally now to FIG. 2, another example of the system 10 and method is representatively illustrated. In this example, the sensor 20 is positioned at a selected level with respect to the vessel 14.

When a level of the substance 12 reaches the sensor 20, thermal conductivity measurements made by the sensor will change. Similarly, if the level of the substance 12 is above the sensor 20, and then the level of the substance drops to below the sensor, the thermal conductivity measurements made by the sensor will change. Thus, the sensor 20 measurements can be used to determine when the level of the substance 12 increases or decreases past a particular point.

In the FIG. 2 example, the sensor 20 can similarly be used to determine when a level of the substance 22 increases or decreases past a particular point. Indeed, the sensor 20 can be used to determine when a level of an interface 26 between the substances 12, 22 increases or decreases past a particular point.

Figure 3:
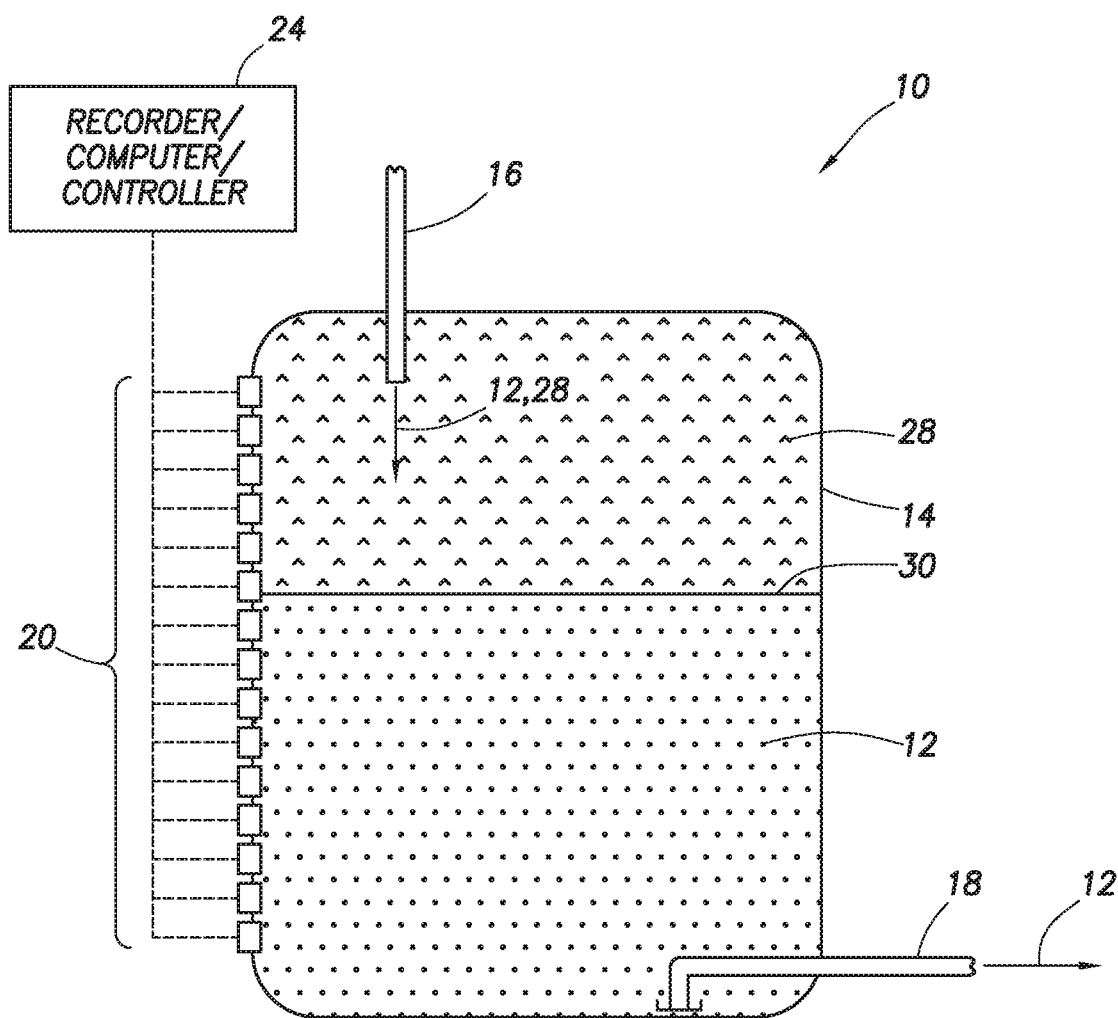

Referring additionally now to FIG. 3, another example of the system 10 and method is representatively illustrated. In this example, multiple individual thermal conductivity sensors 20 are distributed vertically along the vessel 14. In addition, another substance 28 is delivered into the vessel 14 via the conduit 16.

For example, the vessel 14 could be used for separating the substances 12, 28 therein. As depicted in FIG. 3, the substance 28 is less dense as compared to the substance 12, and so the substance 28 collects in a top of the vessel 14. The substance 12 collects in a bottom of the vessel, where it is discharged via the conduit 18.

Using the multiple distributed sensors 20, a level of an interface 30 between the substances 12, 28 can be readily determined in real time by, for example, comparing the measurements made by the sensors 20 to each other and looking for a change in the measurements from one sensor to another. Likewise, levels of each of the substances 12, 28 can be determined in real time.

Note that it is not necessary for the sensors 20 to be only vertically distributed. For example, if the vessel 14 is inclined, the sensors 20 may also be inclined. As another example, if the substances 12, 28 would separate other than vertically (such as, in a centrifuge, radially or horizontally, etc.), then the sensors 20 may be distributed in other orientations. Thus, the scope of this disclosure is not limited to any particular configuration or distribution of the sensors 20.

Figure 4:
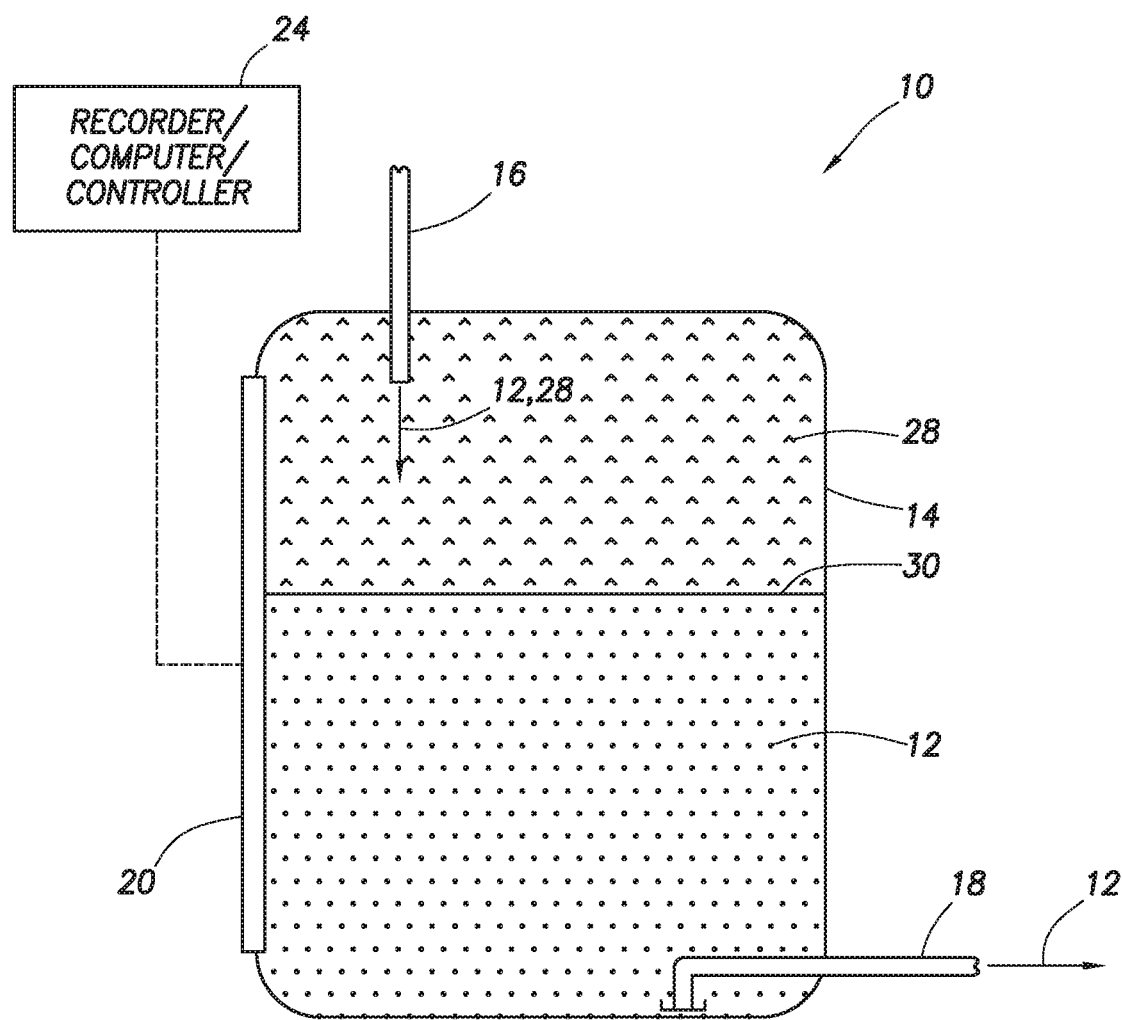

Referring additionally now to FIG. 4, another example of the system 10 and method is representatively illustrated. In this example, the sensor 20 is elongated, so that the single sensor can detect a change in thermal conductivity along its length, to thereby determine the level of the interface 30 between the substances 12, 28 in real time. Likewise, levels of each of the substances 12, 28 can be determined in real time using the single sensor 20.

Figure 5:
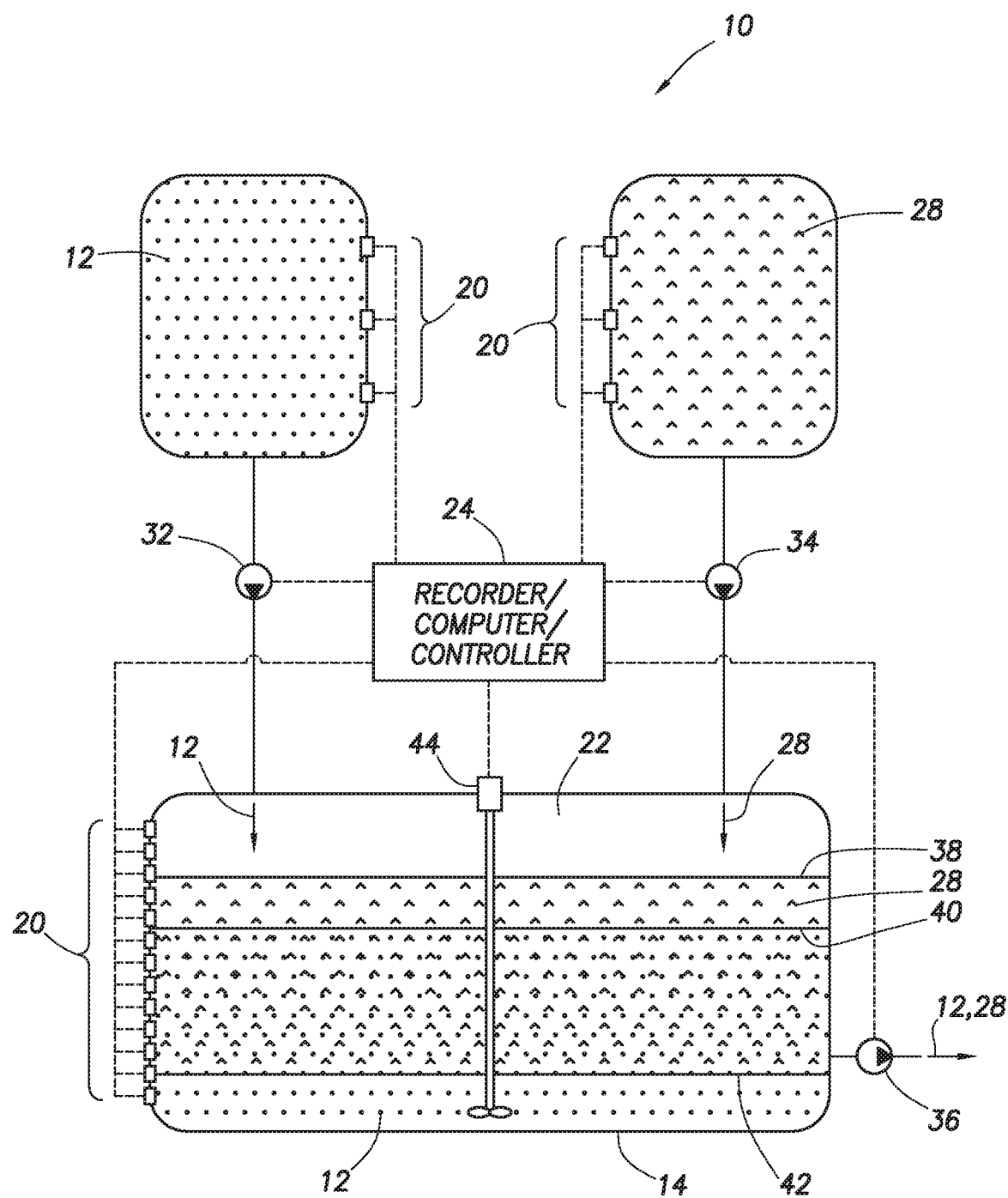

Referring additionally now to FIG. 5, another example of the system 10 and method is representatively illustrated. In this example, the monitoring device 24 is used to control supplies of the substances 12, 28 into the vessel 14, and to control discharge of a mixture of the substances 12, 28 from the vessel.

Specifically, the monitoring device 24 is connected to a pump, valve or other process control device 32 (or combination of process control devices) for supplying the substance 12 to the vessel 14, to another pump, valve or other process control device 34 (or combination of process control devices) for supplying the substance 28 to the vessel, and to yet another pump, valve or other process control device 36 (or combination of process control devices) for discharging the mixture of substances 12, 28 from the vessel.

Thermal conductivity sensors 20 are used to determine a level of the substance 12 supply, to determine a level of the substance 28 supply, and to determine levels of various substance interfaces 38, 40, 42 in the vessel 14. Based on measurements made by the sensors 20, flow rates of the substances 12, 28 into the vessel 14 may be individually adjusted (for example to achieve a desired density of the mixture of substances, to ensure continuous delivery of the substances to the vessel, etc.), and a flow rate of the mixture from the vessel may be adjusted.

Other types of process control devices can be controlled using the monitoring device 24. In the FIG. 5 example, a mixer 44 can be controlled by the monitoring device 24 to ensure that the substances 12, 28 discharged from the vessel 14 are adequately mixed. Thus, the scope of this disclosure is not limited to use of the monitoring device 24 to control operation of any particular type or combination of process control devices.

Referring additionally now to FIG. 6, another example of the system 10 and method is representatively illustrated. In this example, thermal conductivity measurements made by a sensor 20a at the vessel 14 are compared to thermal conductivity measurements made by a sensor 20b at another vessel 46, in order to determine whether the same substance is in both vessels.

The vessel 46 is connected in the system 10, so that it is substantially certain that the substance 12 will be present in that vessel. For example, a continuous supply of the substance 12 could be provided to the vessel 46 from the conduit 16.

If thermal conductivity measurements made by the sensor 20a at the vessel 14 match (or are at least substantially equal to) thermal conductivity measurements made by the sensor 20b, then it can be readily determined that the substance 12 is present in the vessel 14. In addition, techniques such as those discussed above in relation to the examples of FIGS. 1-5 can be used with the FIG. 6 example to determine a level of the substance 12 in the vessel 14, a level of one or more interfaces between substances, etc.

It may now be fully appreciated that the above disclosure provides significant advancements to the arts of determining a presence, identity and/or level of a substance in a vessel. In various examples described above, thermal conductivity measurements can be used to identify a particular substance in the system 10, to determine whether a particular substance is present in the vessel 14, and to determine levels of various substances and interfaces between substances.

The above disclosure provides to the art a process control system 10. In one example, the system 10 can include a first vessel 14, and at least one thermal conductivity sensor 20 that measures a thermal conductivity of a first substance 12 at the first vessel 14.

A monitoring device 24 may determine whether the first substance 12 is present in the first vessel 14, based on an output of the thermal conductivity sensor 20. A monitoring device 24 may determine a level of the first substance 12 in the first vessel 14, based on an output of the thermal conductivity sensor 20. A monitoring device 24 may adjust operation of a process control device 32, 34, 36, 44 in response to an output of the thermal conductivity sensor 20.

The "at least one" thermal conductivity sensor 20 can comprise first and second thermal conductivity sensors 20a, 20b. In this example, the first thermal conductivity sensor 20a measures the thermal conductivity of the first substance 12 at the first vessel 14, and the second thermal conductivity sensor 20b measures a thermal conductivity of the first substance 12 at a second vessel 46. A monitoring device 24 compares outputs of the first and second thermal conductivity sensors 20a,b and thereby determines whether the first substance 12 is present in the first vessel 14.

The "at least one" thermal conductivity sensor 20 can comprise multiple distributed thermal conductivity sensors 20. A monitoring device 24 may determine a level of the first substance 12 in the first vessel 14, based on outputs of the thermal conductivity sensors 20. The monitoring device 24 may determine an interface 30 between the first and second substances 12, 28 in the first vessel 14, based on outputs of the thermal conductivity sensors 20.

The system 10 can include a second substance 28 in the first vessel 14, and a monitoring device 24 can determine a position of an interface 30 between the first and second substances 12, 28 in the first vessel 14, based on an output of the thermal conductivity sensor 20.

A method of controlling a process is also provided to the art by the above disclosure. In one example, the method comprises: measuring a thermal conductivity of a first substance 12 at a first vessel 14, and adjusting the process in response to the measuring step.

The method can include determining whether the first substance 12 is present in the first vessel 14, based on the measuring step.

The measuring step can include measuring a thermal conductivity of the first substance 12 at a second vessel 46, and the method can include determining whether the first substance 12 is present in the first vessel 14, based on a comparison of the thermal conductivities measured at the first and second vessels 14, 46.

The method can include determining a level of the first substance 12 in the first vessel 14, based on the measuring step.

The measuring step can include receiving measurements from multiple distributed thermal conductivity sensors 20, and the method can include determining a level of the first substance 12 in the first vessel 14, based on the measuring step.

The method may comprise determining an interface 30 between the first substance 12 and a second substance 28 in the first vessel 14, based on the measuring step.

The measuring step may include receiving measurements from multiple distributed thermal conductivity sensors 20, and the method can comprise determining an interface 30 between the first substance 12 and a second substance 28 in the first vessel 14, based on the measuring step.

A process control system 10 described above can include a first vessel 14, at least one thermal conductivity sensor 20 that measures a thermal conductivity of a first substance 12 at the first vessel 14, a monitoring device 24 that receives an output of the thermal conductivity sensor 20, and a process control device 32, 34, 36, 44 that is adjusted in response to the thermal conductivity sensor output.

Although various examples have been described above, with each example having certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Although each example described above includes a certain combination of features, it should be understood that it is not necessary for all features of an example to be used. Instead, any of the features described above can be used, without any other particular feature or features also being used.

It should be understood that the various embodiments described herein may be utilized in various orientations, such as inclined, inverted, horizontal, vertical, etc., and in various configurations, without departing from the principles of this disclosure. The embodiments are described merely as examples of useful applications of the principles of the disclosure, which is not limited to any specific details of these embodiments.

The terms "including," "includes," "comprising," "comprises," and similar terms are used in a non-limiting sense in this specification. For example, if a system, method, apparatus, device, etc., is described as "including" a certain feature or element, the system, method, apparatus, device, etc., can include that feature or element, and can also include other features or elements. Similarly, the term "comprises" is considered to mean "comprises, but is not limited to."

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of this disclosure. For example, structures disclosed as being separately formed can, in other examples, be integrally formed and vice versa. Accordingly, the foregoing detailed description is to be clearly understood as being given by way of illustration and example only, the spirit and scope of the invention being limited solely by the appended claims and their equivalents.

What is claimed is:

1. A process control system for processing a first substance, comprising:

a first vessel with the first substance containable within the first vessel;

a first plurality of heat transfer property sensors distributed along the first vessel to measure a heat transfer property of the first substance in the first vessel; and a monitoring device in communication with the first plurality of heat transfer property sensors and configured to identify the first substance in the first vessel based on outputs of only the first plurality of heat transfer property sensors, wherein the monitoring device is operable to determine a level of the first substance in the first vessel, based on outputs of only the first plurality of heat transfer property sensors.

2. The system of claim 1, further comprising a second plurality of heat transfer property sensors distributed along a second vessel to measure a second heat transfer property in the second vessel, and wherein the monitoring device is configured to compare outputs of only the first and second plurality of heat transfer property sensors to determine whether the first substance is present in the first vessel.

3. The system of claim 1, further comprising a second substance in the first vessel, and wherein the monitoring device is configured to determine a position of an interface between the first and second substances in the first vessel based on the outputs of only the first plurality of heat transfer property sensors.

4. The system of claim 1, wherein the monitoring device is operable to adjust operation of a process control device in response to the outputs of the first plurality of heat transfer property sensors.

5. The system of claim 1 for also processing a second substance, further comprising:
a second vessel in fluid communication with the first vessel and the first substance is also containable within the second vessel;
a second plurality of heat transfer property sensors distributed along the second vessel to measure a second heat transfer property in the second vessel;
a third vessel in fluid communication with the first vessel and a second substance containable within the third vessel; and
a third plurality of heat transfer property sensors distributed along the third vessel to measure a third heat transfer property in the third vessel;
wherein the second substance is also containable within the third vessel;
wherein the monitoring device is in connection with the second plurality of heat transfer property sensors and third plurality of heat transfer property sensors, and the monitoring device is configured to determine a second level of the first substance in the second vessel, a third level of the second substance in the third vessel, a fourth level of the second substance in the first vessel, and the location of an interface between the first substance and the second substance in the first vessel, based on the outputs of only the first plurality of heat transfer property sensors, second outputs of only the second plurality of heat transfer property sensors, and third outputs of only the third plurality of heat transfer property sensors.

6. The system of claim 5, further comprising a mixer positioned in the first vessel and operable to mix the first substance and second substance, and operation of the mixer adjustable based on outputs of the first plurality of heat transfer property sensors and the second plurality of heat transfer property sensors.

7. The system of claim 5, further comprising a plurality of process control devices adjustable in response to outputs of the first plurality of heat transfer property sensors, the second plurality of heat transfer property sensors, and the third plurality of heat transfer property sensors, to selectively adjust flow rates of the first substance into or out of the first vessel or second vessel or flow rates of the second substance into or out of the first vessel or third vessel.

8. The system of claim 1, wherein a process control device is controllable by the monitoring device in response to the outputs of the first plurality of heat transfer property sensors to ensure that the first and second substances are mixed in the first vessel.

9. A method of controlling a process, the method comprising:
measuring a first heat transfer property of a first substance in a first vessel via a first plurality of thermal heat transfer property sensors distributed along the first vessel;
determining, with a monitoring device, a level of the first substance in the first vessel based on the measuring of only the first plurality of heat transfer property sensors;
identifying, with the monitoring device, the first substance in the first vessel based on the measuring of only the first plurality of heat transfer property sensors; and
adjusting the process in response to the measuring of the first plurality of heat transfer property sensors, wherein adjusting the process comprises at least one of adjusting a flow rate of the first substance into or out of the first vessel or adjusting an operation of a mixer in the first vessel.

10. The method of claim 9, wherein the measuring further comprises measuring a second heat transfer property at a second vessel, and further comprising determining whether the first substance is present in the first vessel and the second vessel, based on a comparison of the first heat transfer property and the second heat transfer property.

11. The method of claim 9, further comprising determining an interface between the first substance and a second substance in the first vessel, based on the measuring.

12. The method of claim 9, further comprising discharging the mixture from the first vessel.

13. The method of claim 9, further comprising:
measuring a third heat transfer property of the first substance in a second vessel via a second plurality of heat transfer property sensors distributed along the second vessel;
measuring a fourth heat transfer property of the second substance in a third vessel via a third plurality of heat transfer property sensors distributed along the third vessel;
determining, with the monitoring device, a second level of the first substance in the second vessel based on the measuring of only the second plurality of heat transfer property sensors and a second level of the second substance in the third vessel based on the measuring of only the third plurality of heat transfer property sensors; and
selectively adjusting a plurality of process control devices with the monitoring device in response to outputs of the first, second, and third plurality of heat transfer property sensors to adjust flow rates of the first substance into or out of the first vessel or the second vessel or flow rates of the second substance into or out of the first vessel or the third vessel.

14. A process control system for processing a first substance, comprising:

a first vessel;

a thermal conductivity sensor that measures a thermal conductivity of the first substance at the first vessel, wherein the monitoring device is operable to determine a level of the first substance in the first vessel, based on the output of only the thermal conductivity sensor;

a monitoring device that receives an output of the thermal conductivity sensor and, based on the output of only the thermal conductivity sensor, is operable to identify the first substance in the first vessel; and a process control device adjustable in response to the thermal conductivity sensor output to adjust a flow rate of the first substance into or out of the first vessel.

15. The system of claim 14, further comprising a second thermal conductivity sensor that measures a thermal conductivity of the first substance at a second vessel, and wherein the monitoring device is operable to compare outputs of only the first and second thermal conductivity sensors and thereby determine whether the first substance is present in the first vessel.

16. The system of claim 14 for also processing a second substance, further comprising the second substance containable in the first vessel, and wherein the monitoring device is operable to determine a position of an interface between the first and second substances in the first vessel based only on the output of the thermal conductivity sensor.

17. The system of claim 14, wherein the second process control device comprises a mixer positioned in the first vessel to mix the first substance and second substance into a mixture, and wherein the operation of the mixer is adjustable based on outputs of the first plurality of thermal conductivity sensors and the second plurality of thermal conductivity sensors.

18. The system of claim 14, further comprising:

a second vessel with the first substance containable within the second vessel;

a second plurality of thermal conductivity sensors distributed along the second vessel to measuring a third thermal conductivity of the first substance in the second vessel;

a third vessel with the second substance containable within the third vessel;

a third plurality of thermal conductivity sensors distributed along the third vessel to measure a fourth thermal conductivity of the second substance in the third vessel via;

the monitoring device in communication with the second and third plurality of thermal conductivity sensors and configured to determine a second level of the first substance in the second vessel based on outputs of only the second plurality of thermal conductivity sensors and a second level of the second substance in the third vessel based on outputs of only the third plurality of thermal conductivity sensors; and additional process control devices adjustable by the monitoring device in response to the outputs of the second and third plurality of thermal conductivity sensors to adjust flow rates of the first substance into or out of the first vessel or the second vessel or flow rates of the second substance into or out of the first vessel or the third vessel.

* * * * *

UNITED STATES PATENT AND TRADEMARK OFFICE
CERTIFICATE OF CORRECTION

PATENT NO. : 10,599,164 B2
APPLICATION NO. : 15/128768
DATED : March 24, 2020
INVENTOR(S) : Katerina V. Newman et al.

Page 1 of 1

It is certified that error appears in the above-identified patent and that said Letters Patent is hereby corrected as shown below:

In the Claims

Column 7, Lines 64-65 In Claim No. 6:
"operation of the mixer adjustable based on outputs of the first --"
Should read:
"operation of the mixer being adjustable based on outputs of the first --".

Column 8, Lines 17-19 In Claim No. 9:
"a first vessel via a first plurality of thermal heat transfer property sensors distributed along the first vessel;--"
Should read:
"a first vessel via a first plurality of heat transfer property sensors distributed along the first vessel --".

Signed and Sealed this
Twenty-sixth Day of May, 2020

Andrei Iancu
*Director of the United States Patent and Trademark Office*